(12) United States Patent
Ozaki

(10) Patent No.: US 6,298,111 B1
(45) Date of Patent: Oct. 2, 2001

(54) X-RAY COMPUTED TOMOGRAPHY APPARATUS

(75) Inventor: Masahiro Ozaki, Otawara (JP)

(73) Assignee: Kabushiki Kaisha Toshiba, Kawasaki (JP)

( * ) Notice: Subject to any disclaimer, the term of this patent is extended or adjusted under 35 U.S.C. 154(b) by 0 days.

(21) Appl. No.: 09/325,045

(22) Filed: Jun. 3, 1999

(30) Foreign Application Priority Data

Jun. 4, 1998 (JP) .................................................. 10-156364

(51) Int. Cl.$^7$ .................................................. G01N 23/00
(52) U.S. Cl. .................................. 378/8; 378/114; 378/16
(58) Field of Search ........................ 378/8, 114, 20, 378/16, 117, 101, 4, 15

(56) References Cited

U.S. PATENT DOCUMENTS

| 4,382,184 | * | 5/1983 | Wernikoff | 378/37 |
| 4,547,892 | * | 10/1985 | Richey et al. | 378/8 |
| 4,868,747 | * | 9/1989 | Mori et al. | 364/413.18 |
| 5,224,141 | * | 6/1993 | Yassa et al. | 378/99 |
| 5,526,442 | * | 6/1996 | Baba et al. | 382/132 |
| 5,594,772 | * | 1/1997 | Toki et al. | 378/144 |
| 5,687,737 | * | 11/1997 | Branham et al. | 128/710 |
| 5,751,782 | | 5/1998 | Yoshitome . | |
| 5,832,051 | * | 11/1998 | Lutz | 378/8 |

FOREIGN PATENT DOCUMENTS

| 2-6530 | 2/1990 | (JP) . |
| 5-3867 | 1/1993 | (JP) . |
| 9-24045 | 1/1997 | (JP) . |

* cited by examiner

Primary Examiner—David P. Porta
Assistant Examiner—Irakli Kiknadze
(74) Attorney, Agent, or Firm—Oblon, Spivak, McClelland, Maier & Neustadt, P.C.

(57) ABSTRACT

An X-ray computed tomography apparatus includes an X-ray tube, a high voltage generator for applying a high voltage to the X-ray tube to generate X-rays from the X-ray tube, a detector for detecting X-rays coming from the X-ray tube through a subject, a reconstruction processor for reconstructing a tomogram on the basis of projection data detected by the detector, and an electrocardiograph for measuring an electrocardiogram associated with the subject. This apparatus also includes a means for stopping irradiation of the X-rays on the subject in a specific period in a cardiac cycle of the subject, and applying the X-rays onto the subject in a period other than the specific period on the basis of the electrocardiogram. In a cardiac cycle, the dose of X-rays is reduced by the amount corresponding to the specific period as compared with the prior art in which the subject is continuously irradiated with X-rays. In addition, since the X-ray intensity in periods other than specific periods can be set to be higher than that in the prior art, a deterioration in image quality can be suppressed.

27 Claims, 7 Drawing Sheets

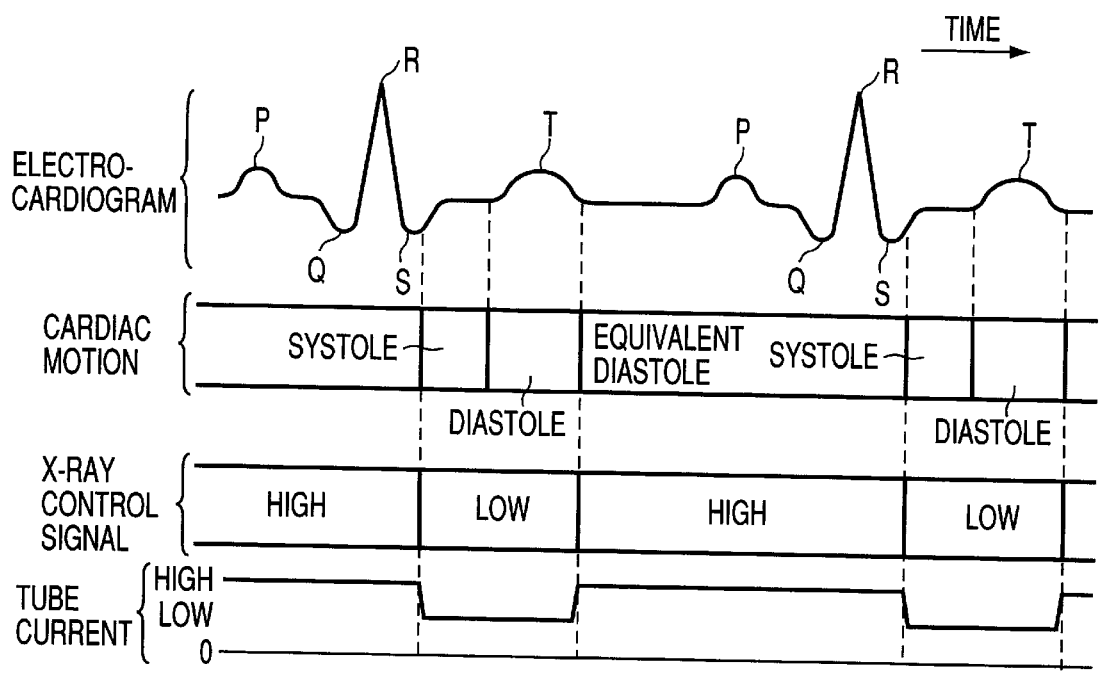
F I G. 11
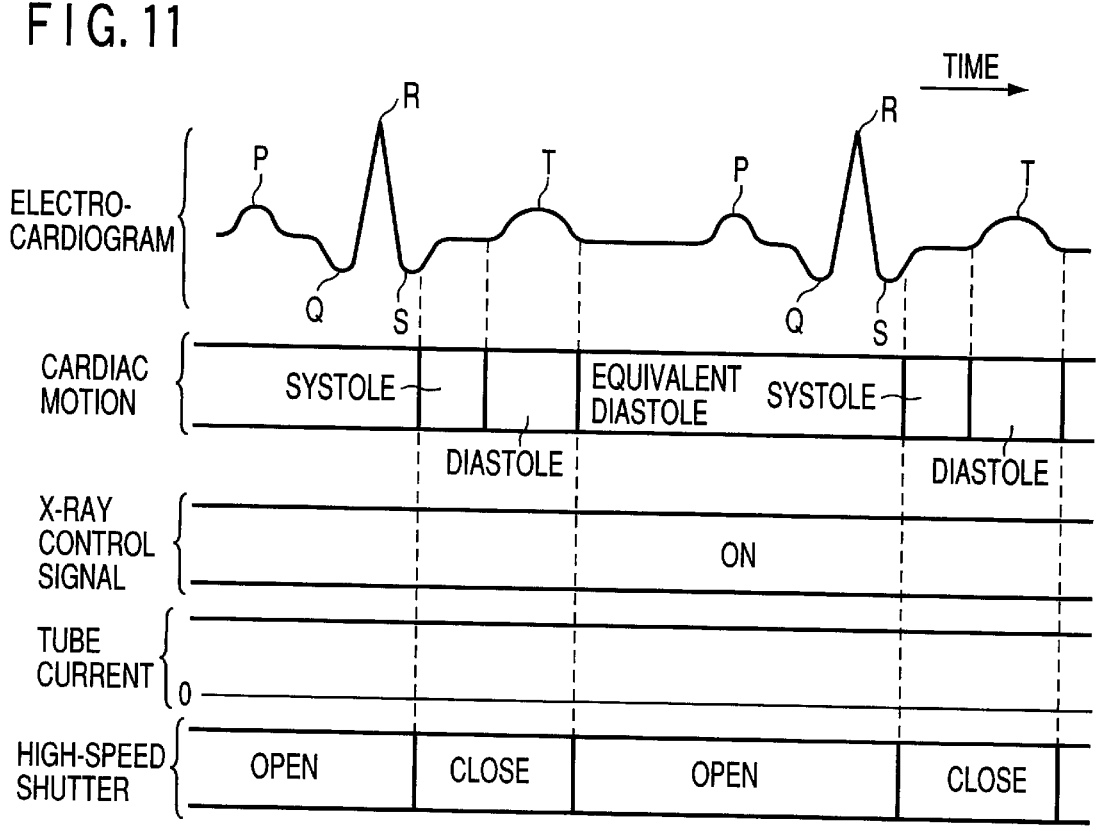
F I G. 13

X-RAY COMPUTED TOMOGRAPHY APPARATUS

BACKGROUND OF THE INVENTION

The present invention relates to an X-ray computed tomography apparatus for reconstructing the image, i.e., a tomogram, of a slice of an inner portion of a subject on the basis of projection data on the subject in many directions.

Many recent X-ray computed tomography apparatuses have an electrocardiographic synchronization function. As shown in FIG. 1, with an electrocardiogram, characteristic waves such as P, Q, R, S, and T waves can be captured. One cardiac cycle is divided into a systole A, a diastole B, and equivalent diastoles C, D, and E. The volume of the heart varies greatly in the systole A and the diastole B, but varies slightly in the equivalent diastoles C, D, and E.

According to the electrocardiographic synchronization function, for example, projection data is acquired a predetermined period of time after the R wave. This data acquisition operation is repeated to obtain, for example, 360° projection data in different projecting directions during a period during which the volume of the heart remains almost the same. A tomogram having no artifact caused by variations in the volume of the heart can be reconstructed on the basis of this obtained projection data.

This electrocardiographic synchronization function, however, demands a very long scanning time. Assume that a tomogram in the systole A is obtained by an apparatus with 750 msec/rotation. Since the systole A is generally 200 msec, a period of time four times a cardiac cycle is required to obtain 360° projection data in the systole A. Since the cardiac cycle is generally one sec, the scanning time is as long as four sec.

For this reason, the subject must be kept exposed to X-rays for a period as long as four sec. In addition, if the X-ray intensity is decreased to reduce the dose of X-rays on the subject, a deterioration in image quality occurs.

BRIEF SUMMARY OF THE INVENTION

It is an object of the present invention to meet both the demands for a reduction in the dose of X-rays and suppression of deterioration in image quality in electrocardiographic synchronization scanning operation of an X-ray computed tomography apparatus.

In the present invention, irradiation of X-rays on a subject is stopped in a specific period in a cardiac cycle, and the subject is irradiated with X-rays in a period other than the specific period in the cardiac cycle. The dose of X-rays can therefore be reduced by the amount corresponding to the specific period in each cardiac cycle as compared with the prior art in which the subject is continuously irradiated with X-rays. In addition, since the X-ray intensity in a period other than the specific period can be set to be higher than that in the prior art, a deterioration in image quality can be suppressed.

Switching operation of irradiation/non-irradiation of X-rays on the subject can be implemented by either X-ray generation/X-ray stop operation of the X-ray tube or opening/closing operation of the shutter.

Furthermore, the dose of X-rays can be reduced even by decreasing the intensity of X-rays applied onto the subject in specific periods without stopping irradiation of X-rays on the subject in the specific periods.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 11 is a timing chart showing another X-ray generating of operation to be performed under the control of the system controller in FIG. 2;

FIG. 13 is a timing chart showing the ON/OFF operation of a high-speed shutter under the control of the system controller in FIG. 12.

DETAILED DESCRIPTION OF THE INVENTION

An X-ray computed tomography apparatus of the present invention will be described in more detail below in conjunction with the preferred embodiments with reference to the views of the accompanying drawing.

First Embodiment

Figure 2:
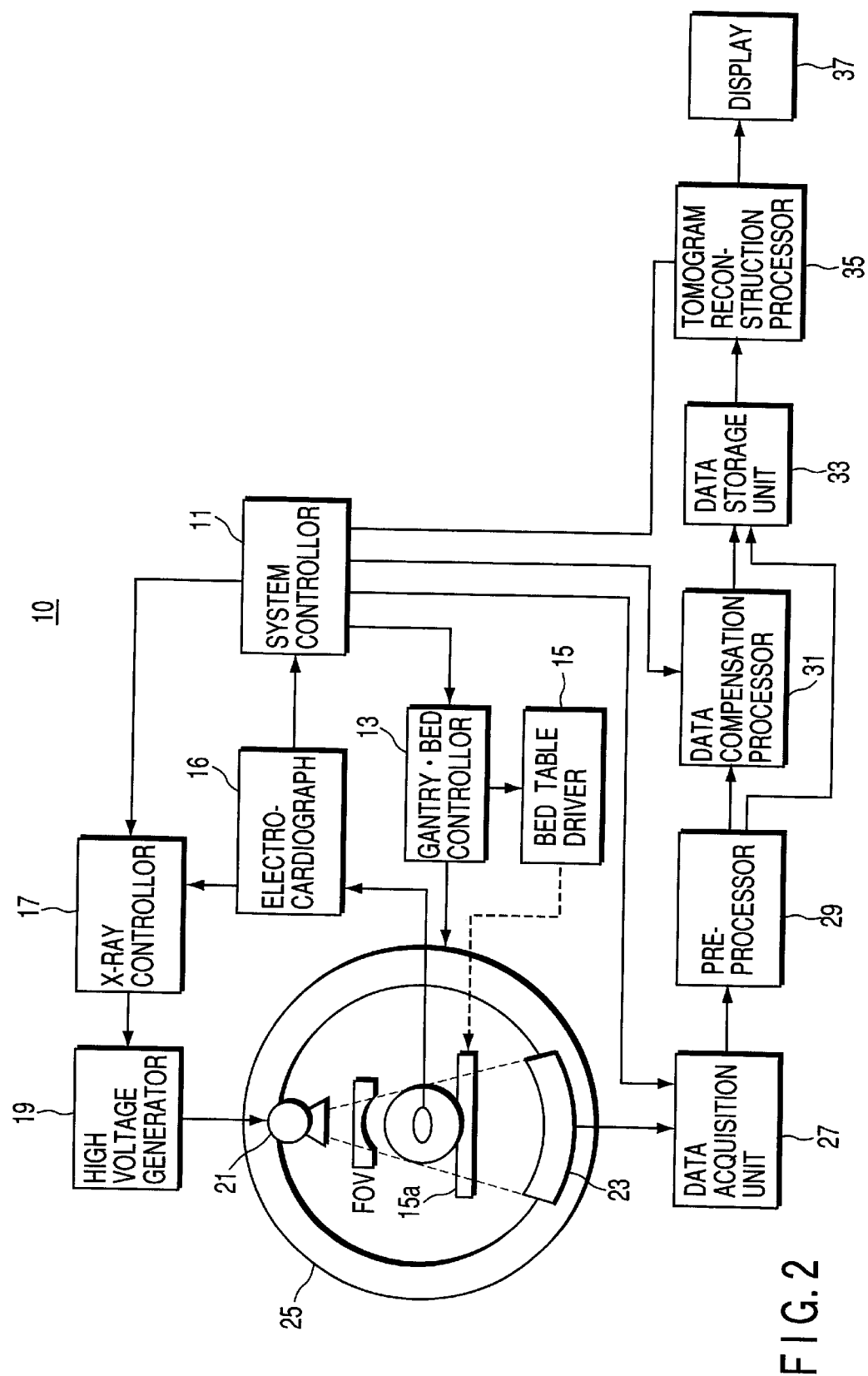
FIG. 2 is a block diagram showing the arrangement of an X-ray computed tomography apparatus according to the first embodiment of the present invention.

FIG. 2 is a block diagram showing the arrangement of the X-ray computed tomography apparatus of the present invention. An X-ray tube 21 and a multi-channel type X-ray detector 23 are mounted on a rotating gantry 25 to oppose each other through a subject on a bed table 15a of a bed. The rotating gantry 25 rotates under the control of a gantry bed controller 13. During rotation of the rotating gantry 25, the X-ray tube 21 and the X-ray detector 23 rotate around the subject. When a high voltage is applied from a high voltage generator 19 to the X-ray tube 21, the X-ray tube 21 generates X-rays. The X-rays that are generated by the X-ray tube 21 and pass through the subject are detected by the X-ray detector 23 and acquired as projection data by a data acquisition unit 27.

The bed table 15a is moved by a bed table driver 15. The gantry-bed controller 13 systematically controls the rotation of the rotating gantry 25 and the movement of the bed table. This systematic control allows the rotating gantry 25 to continuously rotate in synchronism with continuous movement of the bed table. With this operation, the X-ray detector 23 moves along a helical track (see FIG. 4) relative to the subject, and projection data are acquired at a plurality of positions on the helical track, thus realizing so-called helical scanning.

An electrocardiograph 16 detects a weak current produced when the heart of the subject is excited, and outputs a change in detected current over time as an electrocardiogram. A system controller 11 controls scanning operation including generation of X-rays on the basis of the waveform of this electrocardiogram (electrocardiographic synchronization function).

Figure 1:
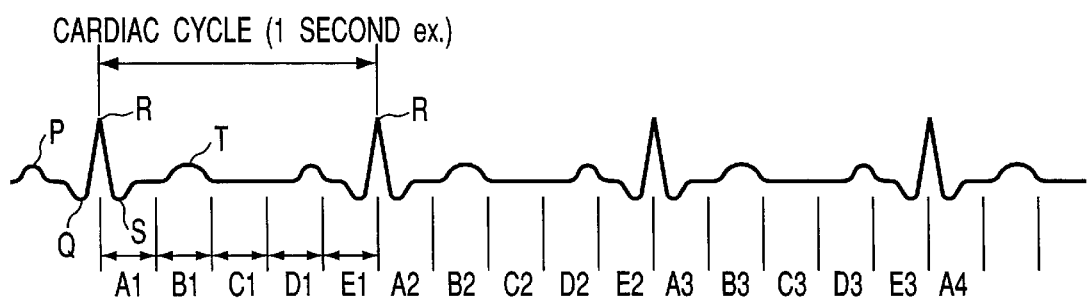
FIG. 1 is a view showing a general electro-cardiogram.
Figure 3:
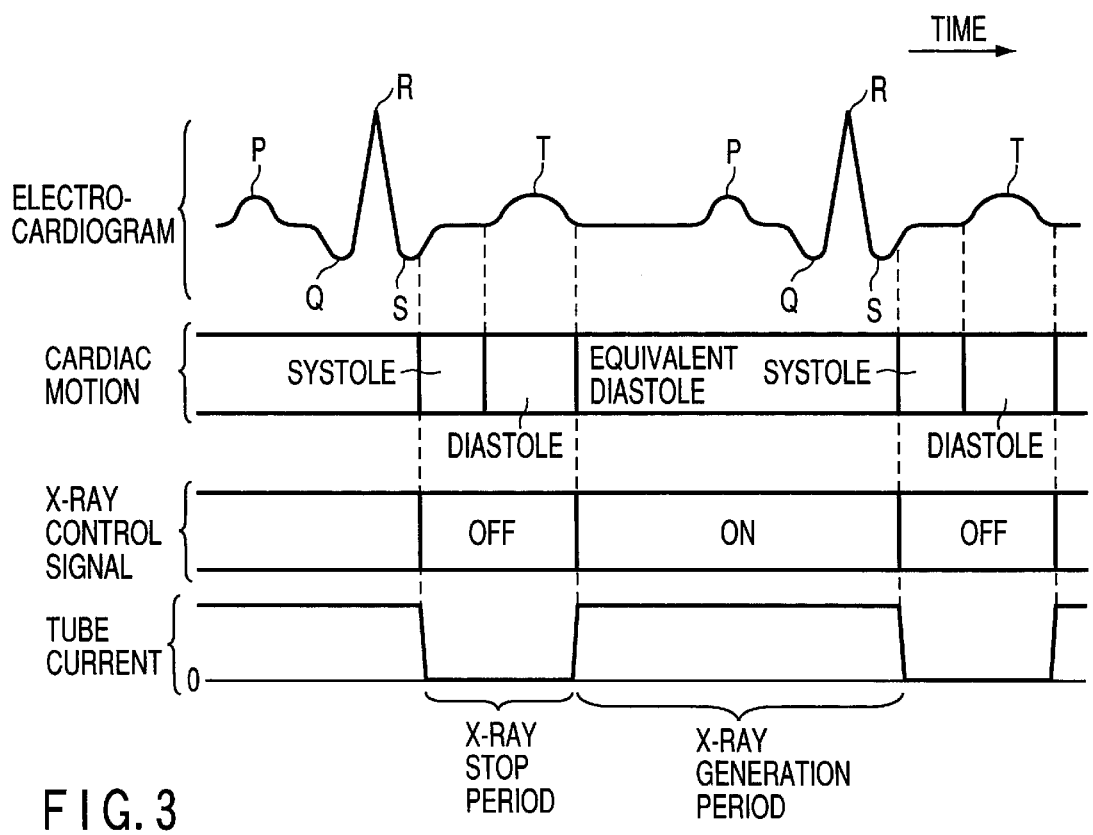
FIG. 3 is a timing chart showing X-ray generating operation to be performed under the control of a system controller in FIG. 2.

FIG. 3 shows an example of an electrocardiogram. As is known, on an electrocardiogram, characteristic waveforms such as P, Q, R, S, and T waves appear in a cardiac cycle. A systole in which the heart contracts comes nearly a predetermined period of time after the R wave, the most characteristic wave. A diastole in which the heart expands follows this systole. The systole and diastole are periods during which the volume of the heart greatly varies. The period that starts immediately after the diastole and ends immediately before the systole in the next cardiac cycle is called an equivalent diastole, in which changes in the volume of the heart are relatively moderate.

The system controller 11 picks up, for example, the R waves from the electrocardiogram. The system controller 11 also obtains the intervals of the R waves, i.e., a cardiac cycle. In addition, the system controller 11 obtains the delay times of systoles with respect to the R waves and the length of the total period of systoles and diastoles (specific period) on the basis of the cardiac cycle. Note that the delay times of systoles with respect to the R waves and the lengths of the total periods of systoles and diastoles are stored in the internal memory (ROM) of the system controller 11 in correspondence with various cardiac cycles.

Figure 4:
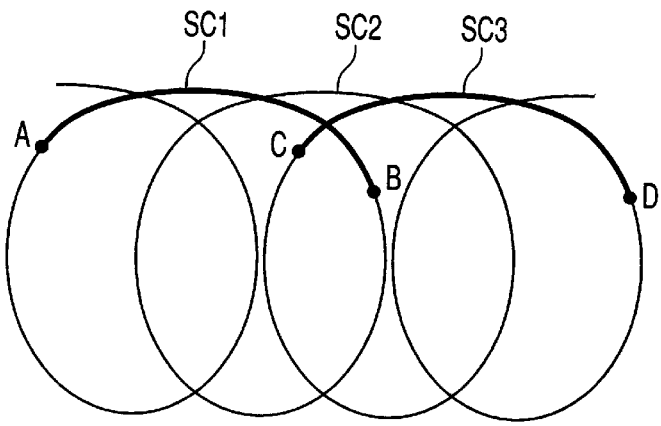
FIG. 4 is a perspective view showing the helical track of an X-ray tube that moves under the control of a gantry bed controller in FIG. 2.

The system controller 11 supplies an X-ray control signal for controlling the generation of X-rays to an X-ray controller 17. For example, when the X-ray control signal is at zero or LOW level, since no high voltage is applied from the high voltage generator 19 to the X-ray tube 21, no X-ray is generated by the X-ray tube 21. In contrast to this, when the X-ray control signal is at HIGH level, since a high voltage is applied from the high voltage generator 19 to the X-ray tube 21, X-rays are generated by the X-ray tube 21. The system controller 11 sets the X-ray control signal at zero or LOW level in the total period (specific period) of a specified systole and diastole, and sets the X-ray control signal at HIGH level in a period (equivalent diastole) other than the specific period. With this operation, X-rays are stopped in the specific period but generated in the period other than the specific period. Therefore, no projection data is detected in the specific period, but projection data is detected in the period other than the specific period. FIG. 4 shows the helical track of the X-ray tube 21. A period A–B and a period C–D are specific periods during which no x-rays are generated.

The system controller 11 controls the rotational speed of the rotating gantry 25 on the basis of the length of each specific period during which no X-ray is generated. This apparatus uses so-called half reconstruction processing for image reconstruction. In this processing, a tomogram is reconstructed from projection data corresponding to 180°+ fan angle. That is, a tomogram can be reconstructed as long as projection data corresponding to 180°+fan angle is acquired.

The system controller 11 therefore sets a rotational speed for the rotating gantry 25 to make the rotating gantry 25 rotate through an angle of (180°+fan angle) or more in an X-ray generation period (other than a specific period), and most preferably, to make the rotating gantry 25 rotate through an angle of (180°+fan angle) in consideration of a reduction in the dose of X-rays. In other words, the system controller 11 set a rotation speed for the rotating gantry 25 to make the rotating gantry 25 rotate through an angle of 360°−(180°+fan angle) or less in a specific period during which no X-ray is generated.

The system controller 11 also supplies the X-ray control signal to the data acquisition unit 27 and a data compensation processor 31. The data acquisition unit 27 amplifies an output current from the X-ray detector 23 and converts it into digital data. Note that the digital data is information called projection data that reflects the X-ray transmittance of the subject. The data acquisition unit 27 acquires only the data detected by the X-ray detector 23 in a period other than a specific period during which X-rays are generated, but does not acquire the data detected by the X-ray detector 23 during an X-ray stop period.

The projection data acquired by the data acquisition unit 27 is subjected to pre-processes such as offset correction and reference correction. The resultant data is supplied to the data compensation processor 31.

The data compensation processor 31 compensates for projection data corresponding to 360°−(180°+fan angle), which has not been acquired, by using the actually acquired projection data corresponding to (180°+fan angle) so as to acquire 360° projection data. This compensation process is common in half reconstruction processing. More specifically, the projection data (reflected data) acquired when the X-ray tube 21 is located on the other side is allocated to projection data to be compensated for.

The projection data generated by the data compensation processor 31 is temporarily stored in a data storage unit 33, together with the actually acquired projection data. A tomogram reconstruction processor 35 reconstructs a tomogram of the subject on the basis of the 360° projection data temporarily stored in the data storage unit 33. A display 37 displays the tomogram of the subject, reconstructed by the tomogram reconstruction processor 35, on a monitor.

The operation of an X-ray computed tomography apparatus having the above arrangement will be described next with reference to the views of the accompanying drawing. First of all, prior to actual acquisition of projection data, the system controller 11 receives an electrocardiogram of the subject like the one shown in FIG. 3 from the electrocardiograph 16, picks up the R waves from this electrocardiogram, and obtains the delay time of a systole and the length of the total period (specific period) of a systole and diastole from the R waves.

Subsequently, projection data is actually acquired by helical scanning. At this time, the rotational speed of the rotating gantry 25 is adjusted to make the rotating gantry 25 rotate through an angle of (180°+fan angle) during an X-ray generation period (other than the specific period). The system controller 11 then picks up the R wave from the electrocardiogram from the electrocardiograph 16, and changes the X-ray control signal from HIGH level, at which X-rays are generated, to zero or LOW level, at which no X-ray is generated, when the delay time obtained in advance has elapsed after the R wave. With this operation, the generation of X-rays is stopped at the beginning of a systole. For example, no X-ray is generated by the X-ray tube 21 in the period A–B and the period C–D in FIG. 4.

Figure 6:
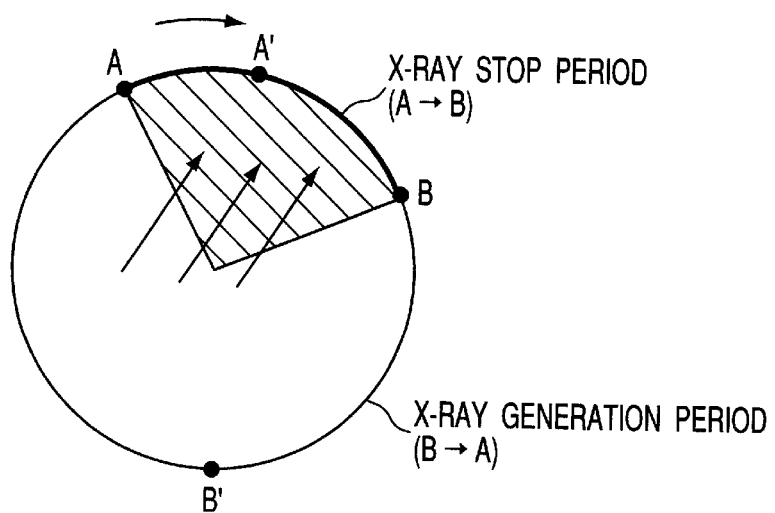
FIG. 6 is a view for explaining half reconstruction processing performed by a tomogram reconstruction processor in FIG. 2.

This X-ray control signal is kept at zero or LOW level for the length of the specific period obtained in advance. This stops the generation of X-rays in the interval between the beginning of a systole and at least the end of a diastole. Thereafter, the level of the X-ray control signal is restored to HIGH level to restart generation of X-rays. X-rays are generated during a period B–B'–A and the generation of X-rays is stopped during a period A–A'–B in FIG. 6. That is, projection data is acquired during the period B–B'–A, but is not acquired during the period A–A'–B.

Figure 5:
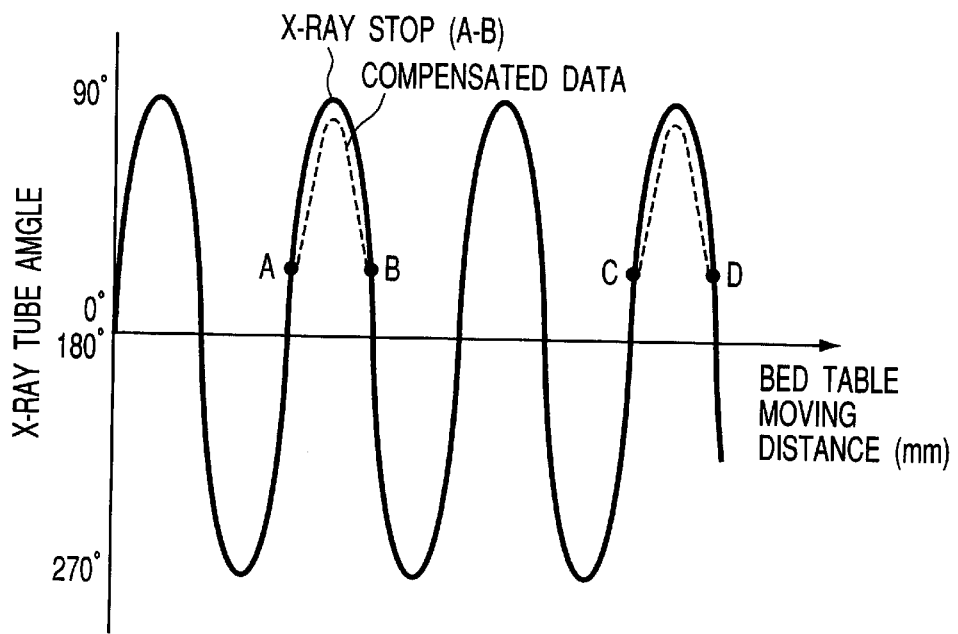
FIG. 5 is a view showing the helical track of the X-ray tube that moves under the control of the gantry bed controller in FIG. 2 when viewed from the above.

FIG. 5 shows the track of the X-ray tube 21 when viewed from above the gantry. Referring to FIG. 5, the abscissa corresponds to the moving distance of the bed table 15a; and the ordinate, the rotational angle of the X-ray tube 21. In this case, the X-ray tube 21 makes one rotation per second, and the bed table 15a moves by 10 mm in a period of one second during which the X-ray tube 21 makes one rotation.

The projection data acquired by the data acquisition unit 27 is sent to the data compensation processor 31 through the preprocessor 29. The data compensation processor 31 recognizes an X-ray stop period on the basis of the X-ray control signal from the system controller 11, and compensates for projection data during this period on the basis of the actually acquired projection data.

Figure 7:
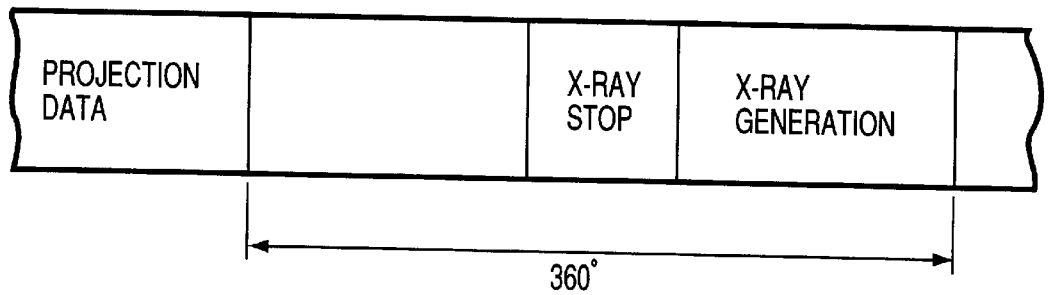
FIG. 7 is a view showing the concept of data compensation processing performed by a data compensation processor in FIG. 2.

In the period between points A and B in FIG. 5, the dotted line represents the compensated projection data. The three arrows in FIG. 6 indicate that projection data in an X-ray stop period is generated by using projection data in an X-ray generation period. FIG. 7 shows projection data in one scanning period (360°).

Figure 8:
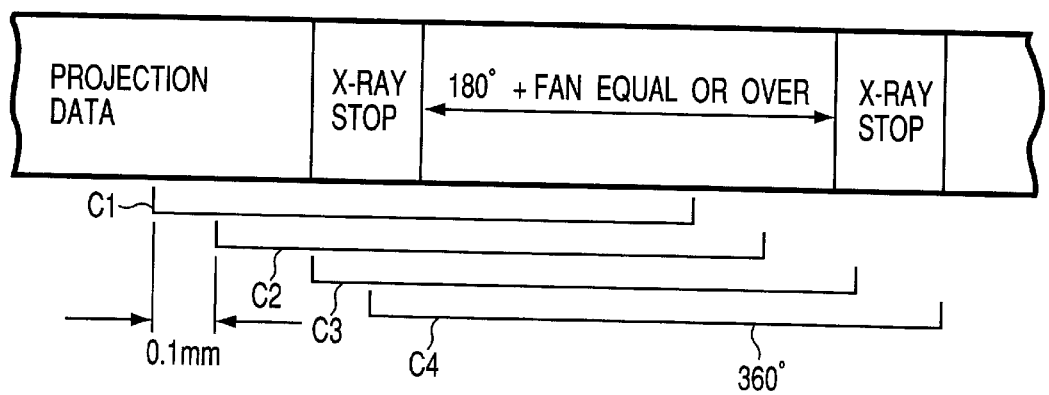
FIG. 8 is a view showing a sequence of tomogram reconstruction processing performed by the tomogram reconstruction processor in FIG. 2.

One tomogram is reconstructed per rotation on the basis of the actually acquired projection data and the compensated projection data, which amount to 360° projection data. As shown in FIG. 8, in high-time-resolution operation of reconstructing one tomogram every time the rotating gantry 25 rotates through 30°, continuous projection data corresponding to 180°+fan angle may not be acquired in some cases (C1, C2). In such a case, data is compensated, as needed.

Figure 9:
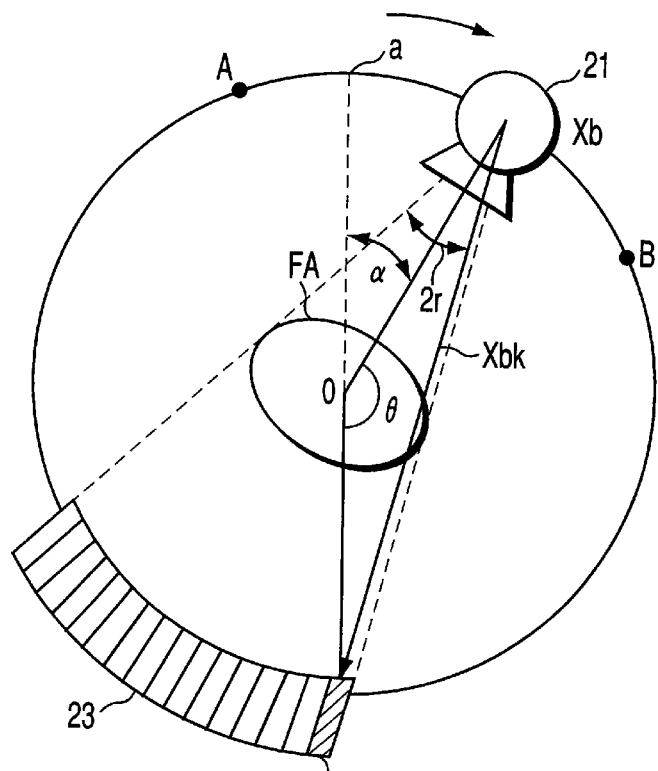
FIG. 9 is a view showing the geometry of the X-ray tube and the like during an X-ray stop period in the first embodiment.
Figure 10:
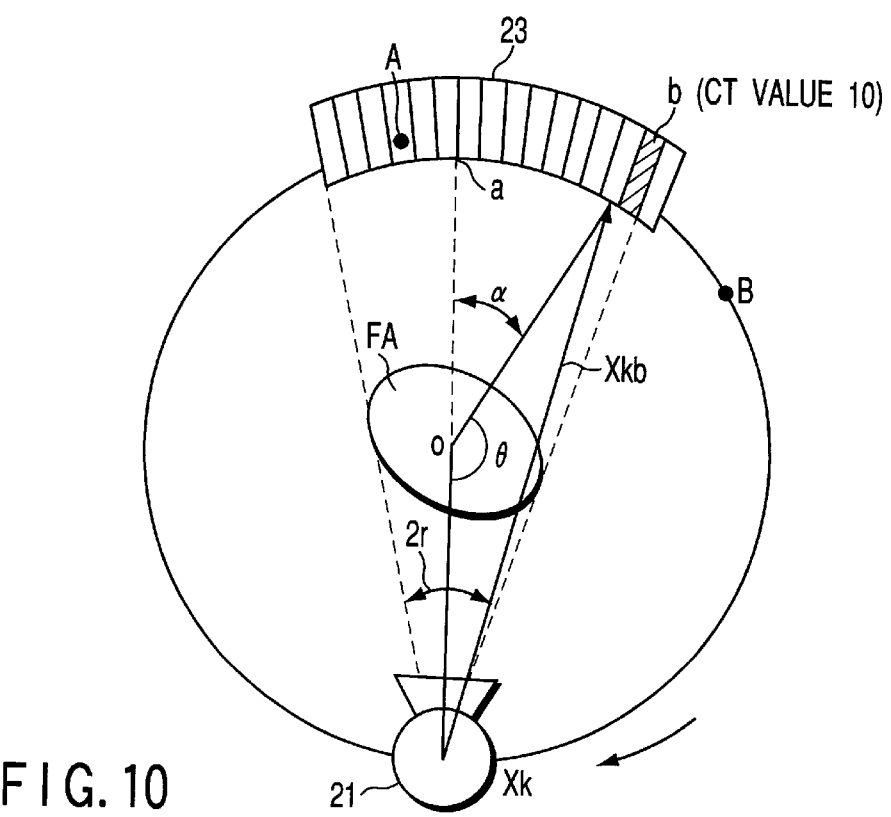
FIG. 10 is a view showing the geometry of the X-ray and the like during an X-ray generation period in the first embodiment.

A compensation process for projection data will be described next with reference to FIGS. 9 and 10. Referring to FIGS. 9 and 10, a point a is the cardinal point of the X-ray tube 21. The generation of X-rays is stopped during a period from a point A, the point a, a point b, to a point B, but X-rays are generated during a period B–A. Let α be the view angle when the X-ray tube 21 is at the point b, and 2γ be the fan angle representing the spread angle of an X-ray beam. The position of an X-ray focal point is represented by Xb when the X-ray tube 21 is located at the point b. The angle defined by the X-ray focal point position Xb, a rotation center O, and a detection channel k is represented by θ. Assume that an X-ray irradiating path connecting the X-ray focal point position Xb and the detection channel k is represented by Xbk, and the CT value detected through the detection channel k is 10.

The generation of data detected through the detection channel k when the X-ray tube 21 is at the point b will be described below. Referring to FIG. 10, when an X-ray focal point Xk of the X-ray tube 21 is located at the position of the channel k in FIG. 9, the channel corresponding to the X-ray focal point position Xb is represented by b. In this case, an X-ray irradiating path connecting the X-ray focal point position Xk and the detection channel b is represented by Xkb, which coincides with the track Xbk of the compensated projection data. In this manner, the CT value of the projection data whose track coincides with or is located nearest to the X-ray irradiating path is allocated to the CT value of compensated projection data. By allocating the CT value of projection data whose track coincides with the X-ray irradiating path to each of the remaining data, the projection data during the X-ray stop period can be compensated for.

Note that there are limitations imposed on data that can be compensated for. The angle at which data can be compensated is defined as follows:

$$360° - (180° + \text{fan angle})$$

If, for example, the fan angle is 45°, the angle becomes 135°.
This angle is converted into a time as follows:

$$\text{scanning speed} \times 135°/360°$$

If, for example, the scanning speed is 0.5 sec/360°, the time corresponding to the angle is 188 msec. The heartbeat rate of a healthy person is about 70 beats/min. The total period of a systole and diastole of the heart is therefore about 200 msec. That is, the time corresponding to the angle almost coincides with the total period of a systole and diastole of the heart.

By applying the compensated data to the total period of the systole and diastole, 360° seamless image can be reconstructed.

The projection data compensated by the data compensation processor 31 and the projection data from the preprocessor 29 are temporarily stored in the data storage unit 33, and the tomogram reconstruction processor 35 reconstructs a tomogram of the subject on the basis of the projection data from the data storage unit 33.

When a first scanning period SC1 comes to an end, a second scanning period SC2 starts. In the second scanning period SC2, however, there is no X-ray stop period. If one scanning period is 0.5 sec, two scanning periods amount to one sec. As a consequence, an X-ray stop period is present in each odd-numbered scanning period. For this reason, as shown in FIGS. 4 and 5, an X-ray stop period A–B is present in the first scanning period SC1, and an X-ray stop period C–D is present in a third scanning period SC3.

When helical scanning is performed in this manner, and the tomogram reconstruction processor 35 reconstructs an image from the resultant helical scan data, 3-D volume data of the heart can be obtained.

As described above, according to the X-ray computed tomography apparatus of this embodiment, the system controller 11 stops the generation of X-rays to the subject until a lapse of a period, in one cardiac cycle, during which the shape of the heart greatly changes, e.g., the total period of a systole and diastole of the heart, in synchronism with the R waves in heartbeat data, on the basis of the electrocardiogram measured by the electrocardiograph 16. This operation can minimize the dose of X-rays on the subject, and also allows electrocardiographic synchronization scanning.

In the X-ray computed tomography apparatus of this embodiment, in particular, since helical scanning is performed, the subject is irradiated with X-rays a plurality of number of times. Owing to X-ray stop periods, however, the dose of X-rays on the subject can be reduced, thus providing great effects.

In addition, since the position of an X-ray stop period changes, X-rays can be applied to a morbid portion regardless of the position of the morbid portion. A clear image can be obtained for the morbid portion. This allows an appropriate diagnosis.

When the data compensation processor 31 generates projection data in a change period, during which the generation of X-rays is stopped, on the basis of projection data in an X-ray generation period, in one scanning period, except for the change period, the tomogram reconstruction processor 35 reconstructs a tomogram of the subject on the basis of the generated projection data in the change period and the projection data in the X-ray generation period. Therefore, a 360° seamless image can be reconstructed, and a clear image can be obtained even in the change period during which the shape of the heart greatly changes.

In addition, the system controller 11 sets a scanning time in one scanning period on the basis of the length of a change period and data in an angle range unnecessary for half reconstruction processing. That is, a 360° seamless image can be reconstructed by properly selecting a scanning time.

The system controller 11 sets the length of an X-ray stop period to be shorter than the time obtained according to equation (1):

$$\text{scan time} \times \{360° - (180° + \text{fan angle})\}/360° \quad (1)$$

More specifically, the data in the angle range unnecessary for half reconstruction processing is divided by 360, and the resultant value is multiplied by the scanning time in one scanning period. Since the length of the change period is set to be smaller than the resultant value, a 360° seamless image can be reconstructed.

As described above, according to this embodiment, the generation of X-rays is stopped in a specific period in a cardiac cycle, and X-rays are generated in a period other than the specific period in the cardiac cycle. Therefore, the subject is irradiated with no X-rays in the specific period but is irradiated with X-rays in only the period other than the specific period in each cardiac cycle. For this reason, the dose of X-rays can be reduced by the amount corresponding to specific periods as compared with the prior art in which the subject is continuously irradiated with X-rays in cardiac cycles.

In addition, since the X-ray intensity in a period other than a specific period can be set to be higher than that in the prior art, a deterioration in image quality can be suppressed.

The present invention is not limited to the embodiment described above. In the embodiment, the present invention is applied to helical scanning. However, the present invention can also be applied to conventional scanning.

This conventional scanning is scanning operation in which an rotating gantry makes one rotation around a target slice. When images of a plurality of slices, e.g., slices A and B, are to be obtained, data is acquired while the rotating gantry makes one rotation around the slice A, and the rotating surface is adjusted to the slice B by moving the bed on which the subject is placed or the X-ray focal point and the detector. Thereafter, data is acquired while the rotating gantry makes one rotation around the subject as in the case of the slice A.

In addition, according to this embodiment, the data compensation processor 31 is externally prepared independently of the tomogram reconstruction processor 35. However, for example, the data compensation processor 31 may be incorporated in the tomogram reconstruction processor 35. In this case, the data compensation processor 31 in the tomogram reconstruction processor 35 may generate projection data in an X-ray stop period in image reconstruction operation. Then, the tomogram reconstruction processor 35 may reconstruct an image by using the projection data in the X-ray stop period.

Furthermore, in this embodiment, single slice CT has been described. However, the present invention may be applied to multi-slice CT with a 2-D detector array having a plurality of arrays of detectors arranged in the axis direction of the subject instead of one array of detectors. According to this multi-slice CT, projection data corresponding to a plurality of slices are acquired in one scanning operation by using the 2-D detector array, and a plurality of tomograms (volume data) can be obtained.

In this embodiment, the system controller 11 generates an X-ray control signal. However, the X-ray controller 17 may directly receive an R wave trigger from the electrocardiograph 16 without the mediacy of the system controller 11, and may generate an X-ray control signal on the basis of the R wave trigger.

In this embodiment, the scanning speed is set to 0.5 sec to make X-ray stop periods fall within the same angle range in every odd-numbered scanning. However, the angle range of an X-ray stop period may be made to change every scanning by arbitrarily setting a scanning speed. This allows execution of scanning operation in accordance with the heart rate of each patient, and hence can reduce the burden on each patient.

Although the X-ray computed tomography apparatus of this embodiment is a third-generation (R/R scheme) CT apparatus, the rotating gantry 25 is not limited to this type. The rotating gantry 25 may be of a so-called fourth-generation (R/S scheme) type having detectors arranged around a subject throughout 360° and allowing only the X-ray tube 21 to rotate. The rotating gantry 25 may be of a so-called fifth-generation (S/S scheme) type having the X-ray tubes 21 arranged around a subject throughout 360° in addition to detectors.

According to the above description, the generation of X-rays is stopped in X-ray stop periods. As shown in FIG. 11, however, the dose of X-rays can be reduced even by setting the X-ray intensity in only specific periods lower than that in other periods while continuously generating X-rays instead of stopping the generation of X-rays.

Second Embodiment

Figure 12:
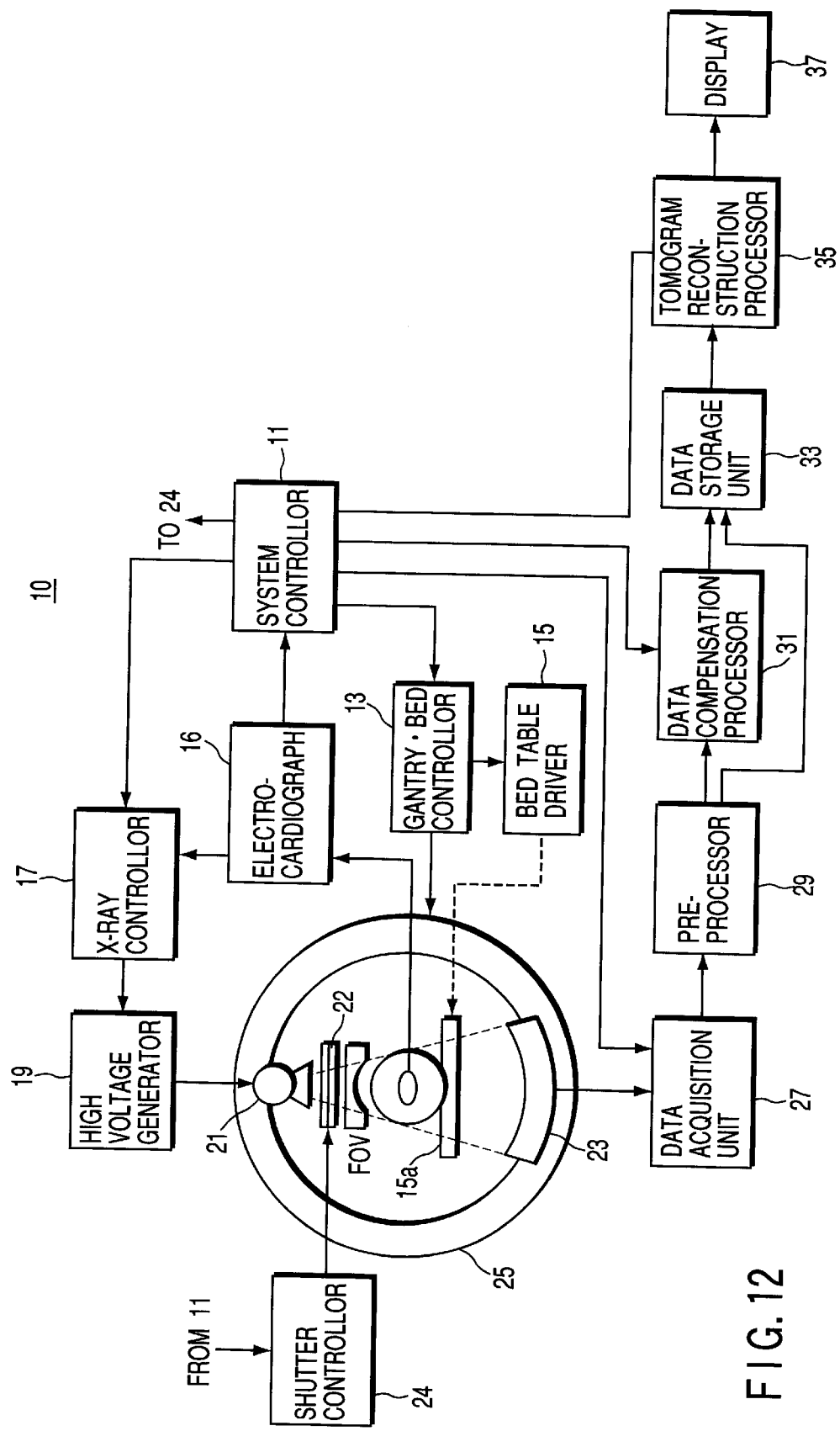
FIG. 12 is a block diagram showing the arrangement of an X-ray computed tomography apparatus according to the second embodiment of the present invention.

FIG. 12 shows the arrangement of an X-ray computed tomography apparatus according to the second embodiment of the present invention. The same reference numerals in FIG. 12 denote the same parts as in FIG. 2, and a description thereof will be omitted. This embodiment includes a high-speed shutter 22 between an X-ray tube 21 and a subject. In this high-speed shutter 22, a plurality of lead plates for shielding against X-rays are geometrically combined to open/close the shutter at a high speed. When the high-speed shutter 22 is open, the subject is irradiated with X-rays. When the high-speed shutter 22 is closed, since X-rays are blocked, the subject is not irradiated with X-rays. This opening/closing operation of the high-speed shutter 22 is controlled by a shutter controller 24 under the control of a system controller 11.

FIG. 13 shows the opening/closing operation of the high-speed shutter controlled by the shutter controller in FIG. 12. As shown in FIG. 13, in this embodiment, X-rays are continuously generated. The high-speed shutter 22 is closed in the sum period (specific period) of systoles and diastoles, but is open in other periods.

According to this embodiment, therefore, the subject is not irradiated with x-rays in a specific period, but is irradiated with X-rays only in a period other than the specific period in a cardiac cycle. For this reason, the dose of X-rays is reduced by the amount corresponding to the specific period in each cardiac cycle as compared with the prior art in which the subject is continuously irradiated with X-rays. In addition, since the X-ray intensity in periods other than specific periods can be set to be higher than that in the prior art, a deterioration in image quality can be suppressed.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An X-ray computed tomography apparatus comprising:
   an X-ray tube;
   a high voltage generator for applying a high voltage to said X-ray tube to generate X-rays from said X-ray tube;
   a detector for detecting X-rays coming from said X-ray tube through a subject;
   a reconstruction processor for reconstructing a tomogram on the basis of projection data detected by said detector;
   an electrocardiograph for measuring an electrocardiogram associated with the subject; and
   means for stopping irradiation of the X-rays on the subject in a specific period in a cardiac cycle of the subject during which cardiac motions of the subject are comparatively great, and for applying the X-rays onto the subject in a period other than the specific period, on the basis of the electrocardiogram.

2. An X-ray computed tomography apparatus comprising:
   an X-ray tube;
   a high voltage generator for applying a high voltage to said X-ray tube to generate X-rays from said X-ray tube;
   a detector for detecting X-rays coming from said X-ray tube through a subject;
   a reconstruction processor for reconstructing a tomogram on the basis of projection data detected by said detector;
   an electrocardiograph for measuring an electrocardiogram associated with the subject; and
   a controller for controlling said high voltage generator on the basis of the electrocardiogram to stop generation of the X-rays in a specific period in a cardiac cycle of the subject during which cardiac motions of the subject are comparatively great, and to generate the X-rays in a period other than the specific period.

3. An apparatus according to claim 2, wherein the specific period includes a systole and diastole in which a shape of a heart greatly changes.

4. An apparatus according to claim 2, further comprising a compensation processor for compensating for projection data corresponding to the specific period on the basis of the projection data detected in the period other than the specific period.

5. An apparatus according to claim 4, wherein said compensation processor allocates reflected data of the detected projection data to the projection data corresponding to the specific period.

6. An apparatus according to claim 4, wherein said compensation processor reconstructs the tomogram on the basis of the compensated projection data and the detected projection data.

7. An apparatus according to claim 2, wherein said reconstruction processor reconstructs the tomogram on the basis of projection data of not less than 180° detected in the period other than the specific period.

8. An apparatus according to claim 7, wherein said controller adjusts the specific period to less than a time required to detect 180° projection data.

9. An apparatus according to claim 2, wherein the projection data is detected at a plurality of positions on a helical track of said X-ray tube with respect to the subject.

10. An X-ray computed tomography apparatus comprising: an X-ray tube;
    a high voltage generator for applying a high voltage to said X-ray tube to generate X-rays from said X-ray tube;
    a detector for detecting X-rays coming from said X-ray tube through a subject;
    a reconstruction processor for reconstructing a tomogram on the basis of projection data detected by said detector;
    an electrocardiograph for measuring an electrocardiogram associated with the subject; and
    a controller for controlling said high voltage generator on the basis of the electrocardiogram to decrease an intensity of the X-rays in a specific period in a cardiac cycle of the subject and increase the intensity of the X-rays in a period other than the specific period.

11. An apparatus according to claim 10, wherein:
    the specific period is a period during which cardiac motions of the subject are comparatively great; and
    the period other than the specific period is a period during which the cardiac motions of the subject are comparatively small.

12. An X-ray computed tomography apparatus comprising:
    an X-ray tube;
    a high voltage generator for applying a high voltage to said X-ray tube to generate X-rays from said X-ray tube;
    a detector for detecting X-rays coming from said X-ray tube through a subject;
    an opening/closing shutter disposed between said X-ray tube and the subject;
    a reconstruction processor for reconstructing a tomogram on the basis of projection data detected by said detector;
    an electrocardiograph for measuring an electrocardiogram associated with the subject; and
    a controller for controlling opening/closing operation of said shutter on the basis of the electrocardiogram to block the X-rays in a specific period in a cardiac cycle of the subject during which cardiac motions of the subject are comparatively great, and to pass the X-rays in a period other than the specific period.

13. An apparatus according to claim 12, wherein the specific period includes a systole and diastole in which a shape of a heart greatly changes.

14. An apparatus according to claim 12, further comprising a compensation processor for compensating for projection data corresponding to the specific period on the basis of the projection data detected in the period other than the specific period.

15. An apparatus according to claim 14, wherein said compensation processor allocates reflected data of the detected projection data to the projection data corresponding to the specific period.

16. An apparatus according to claim 14, wherein said compensation processor reconstructs the tomogram on the basis of the compensated projection data and the detected projection data.

17. An apparatus according to claim 12, wherein said reconstruction processor reconstructs the tomogram on the basis of projection data of about 180° detected in the period other than the specific period.

18. An apparatus according to claim 17, wherein said controller adjusts the specific period to less than a time required to detect 180° projection data.

19. An apparatus according to claim 12, wherein the projection data is detected at a plurality of positions on a helical track of said X-ray tube with respect to the subject.

20. An X-ray computed tomography apparatus comprising:
    an X-ray tube;
    a high voltage generator for applying a high voltage to said X-ray tube to generate X-rays from said X-ray tube;
    a detector for detecting X-rays coming from said X-ray tube through a subject;
    a reconstruction processor for reconstructing a tomogram on the basis of projection data detected by said detector;
    an electrocardiograph for measuring an electrocardiogram associated with the subject;
    a controller for controlling said high voltage generator on the basis of the electrocardiogram to stop generation of the X-rays in a specific period in a cardiac cycle of the subject, and to generate the X-rays in a period other than the specific period; and
    a compensation processor for compensating for projection data corresponding to the specific period on the basis of the projection data detected in the period other than the specific period.

21. An apparatus according to claim 20, wherein said compensation processor allocates reflected data of the detected projection data to the projection data corresponding to the specific period.

22. An apparatus according to claim 20, wherein said compensation processor reconstructs the tomogram on the basis of the compensated projection data and the detected projection data.

23. An X-ray computed tomography apparatus comprising:
    an X-ray tube;
    a high voltage generator for applying a high voltage to said X-ray tube to generate X-rays from said X-ray tube;
    a detector for detecting X-rays coming from said X-ray tube through a subject;
    a reconstruction processor for reconstructing a tomogram on the basis of projection data detected by said detector;
    an electrocardiograph for measuring an electrocardiogram associated with the subject; and
    a controller for controlling said high voltage generator on the basis of the electrocardiogram to stop generation of the X-rays in a specific period in a cardiac cycle of the subject, and to generate the X-rays in a period other than the specific period;
    wherein said reconstruction processor reconstructs the tomogram on the basis of projection data of not less than 180° detected in the period other than the specific period; and
    wherein said controller adjusts the specific period to less than a time required to detect 180° projection data.

24. An X-ray computed tomography apparatus comprising: an X-ray tube;
    a high voltage generator for applying a high voltage to said X-ray tube to generate X-rays from said X-ray tube;
    a detector for detecting X-rays coming from said X-ray tube through a subject;
    an opening/closing shutter disposed between said X-ray tube and the subject;
    a reconstruction processor for reconstructing a tomogram on the basis of projection data detected by said detector;
    an electrocardiograph for measuring an electrocardiogram associated with the subject;
    a controller for controlling opening/closing operation of said shutter on the basis of the electrocardiogram to block the X-rays in a specific period in a cardiac cycle of the subject, and to pass the X-rays in a period other than the specific period; and
    a compensation processor for compensating for projection data corresponding to the specific period on the basis of the projection data detected in the period other than the specific period.

25. An apparatus according to claim 24, wherein said compensation processor allocates reflected data of the detected projection data to the projection data corresponding to the specific period.

26. An apparatus according to claim 24, wherein said compensation processor reconstructs the tomogram on the basis of the compensated projection data and the detected projection data.

27. An X-ray computed tomography apparatus comprising:
    an X-ray tube;
    a high voltage generator for applying a high voltage to said X-ray tube to generate X-rays from said X-ray tube;
    a detector for detecting X-rays coming from said X-ray tube through a subject;
    an opening/closing shutter disposed between said X-ray tube and the subject;
    a reconstruction processor for reconstructing a tomogram on the basis of projection data detected by said detector;
    an electrocardiograph for measuring an electrocardiogram associated with the subject; and
    a controller for controlling opening/closing operation of said shutter on the basis of the electrocardiogram to block the X-rays in a specific period in a cardiac cycle of the subject, and to pass the X-rays in a period other than the specific period;
    wherein said reconstruction processor reconstructs the tomogram on the basis of projection data of about 180° detected in the period other than the specific period; and
    wherein said controller adjusts the specific period to less than a time required to detect 180° projection data.

* * * * *